United States Patent
Kaneko et al.

(10) Patent No.: US 12,310,761 B2
(45) Date of Patent: May 27, 2025

(54) MEDICAL IMAGING APPARATUS INCLUDING BIOLOGICAL SIGNAL PROCESSING SYSTEM, MEDICAL IMAGING SYSTEM, AND BIOLOGICAL SIGNAL PROCESSING METHOD

(71) Applicant: FUJIFILM Healthcare Corporation, Chiba (JP)

(72) Inventors: Yukio Kaneko, Chiba (JP); Hikaru Hanada, Chiba (JP); Toru Shirai, Chiba (JP); Masahiro Takizawa, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 30 days.

(21) Appl. No.: 17/557,233

(22) Filed: Dec. 21, 2021

(65) Prior Publication Data

US 2022/0202376 A1  Jun. 30, 2022

(30) Foreign Application Priority Data

Dec. 28, 2020  (JP) ................................ 2020-219210

(51) Int. Cl.
*A61B 5/00* (2006.01)
*A61B 5/055* (2006.01)
(Continued)

(52) U.S. Cl.
CPC ............ *A61B 5/7292* (2013.01); *A61B 5/055* (2013.01); *A61B 5/1126* (2013.01); *A61B 5/113* (2013.01); *G01S 13/08* (2013.01)

(58) Field of Classification Search
None
See application file for complete search history.

(56) References Cited

U.S. PATENT DOCUMENTS

2009/0253980 A1  10/2009  Wollenweber et al.
2012/0245453 A1*  9/2012  Tryggestad .......... A61B 6/5288
                                                     600/407
(Continued)

FOREIGN PATENT DOCUMENTS

CN      1 01 29 99 67 A    11/2008
CN      1 02 42 13 73 A     4/2012
(Continued)

OTHER PUBLICATIONS

He et al., "A Joint Localization Assisted Respiratory Rate Estimation using IR-UWB Radars," (Aug. 27, 2020) 2020 42nd Annual International Conference of the IEEE Engineering in Medicine & Biology Society (EMBC). (Year: 2020).*

(Continued)

*Primary Examiner* — Joel Lamprecht
*Assistant Examiner* — Ashish S Jasani
(74) *Attorney, Agent, or Firm* — Paul Teng

(57) ABSTRACT

The present invention provides a technique capable of accurately and automatically setting a region of interest for acquiring biological information based on a biological information signal obtained from a subject placed in an examination space in a non-contact manner. A signal analyzing unit of a medical imaging apparatus uses the biological information signal for each of a plurality of regions included in a predetermined range among signals measured by a biological information measuring apparatus to select the region of interest in which movement of the subject is to be acquired among the plurality of regions. The movement of the subject is calculated using the biological information signal measured by the biological information measuring apparatus from the selected region of interest.

14 Claims, 14 Drawing Sheets

(51) Int. Cl.
*A61B 5/11* (2006.01)
*A61B 5/113* (2006.01)
*G01S 13/08* (2006.01)

(56) References Cited

U.S. PATENT DOCUMENTS

2017/0071508 A1* 3/2017 Kaiser .................. H04N 13/204
2020/0043143 A1* 2/2020 Territo .................. G06T 3/0075
2020/0077962 A1* 3/2020 Kartäusch ............. A61B 5/113

FOREIGN PATENT DOCUMENTS

| EP | 3550327 A1 * | 10/2019 | ........... A61N 5/1049 |
| JP | 2010-187723 A | 9/2010 | |
| JP | 2014-179061 A | 9/2014 | |
| JP | 2017-055949 A | 3/2017 | |
| JP | 2018-503455 A | 2/2018 | |
| JP | 6714006 | 6/2020 | |
| WO | WO 2017/047734 A1 | 3/2017 | |

OTHER PUBLICATIONS

Japanese official action dated Sep. 17, 2024 (and English translation thereof) in connection with Japanese Patent Application No. 2020-219210.
Japanese official action dated Jan. 21, 2025 (and English translation thereof) in connection with Japanese Patent Application No. 2020-219210.
Chinese official action dated Oct. 23, 2024 (and English translation thereof) in connection with Chinese Patent Application No. 202111448844.9.
Chinese official action dated Mar. 13, 2025 (and English translation thereof) in connection with Chinese Patent Application No. 202111448844.9.

* cited by examiner

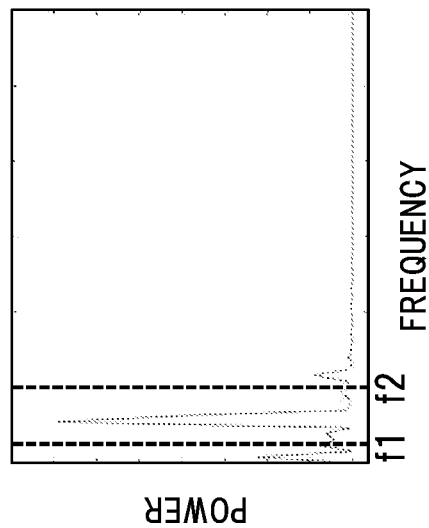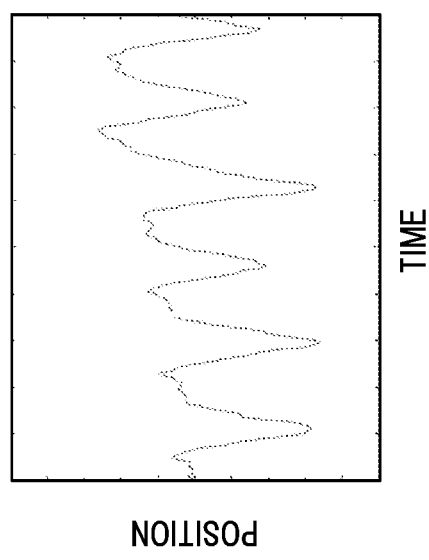

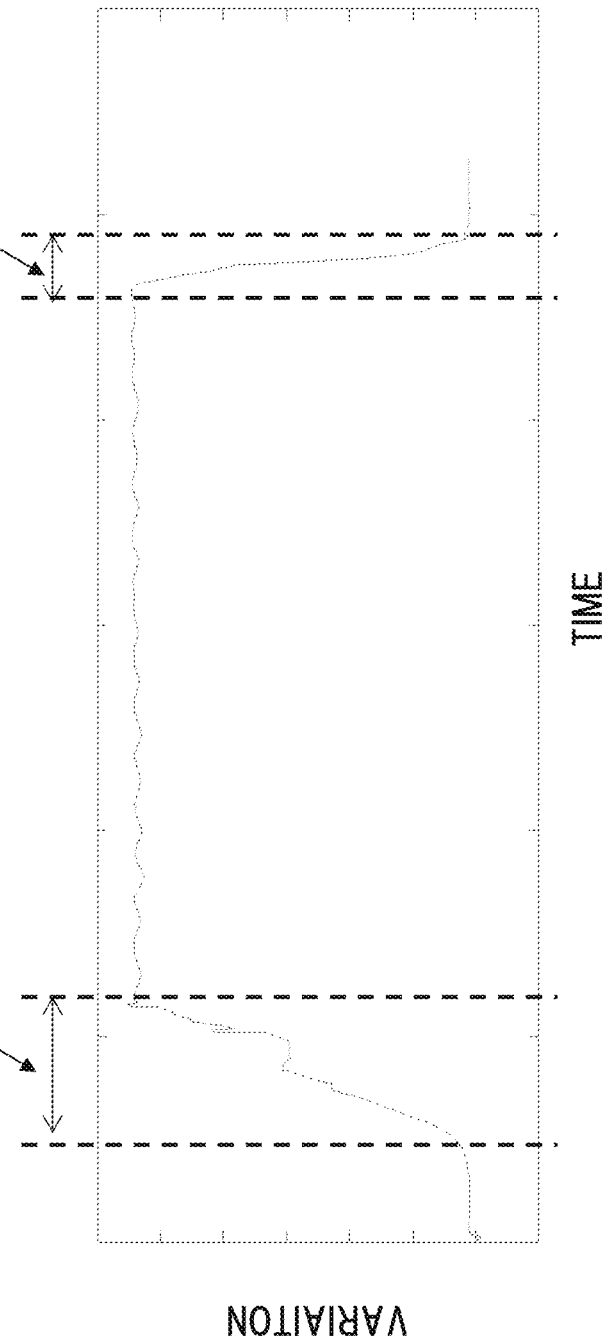

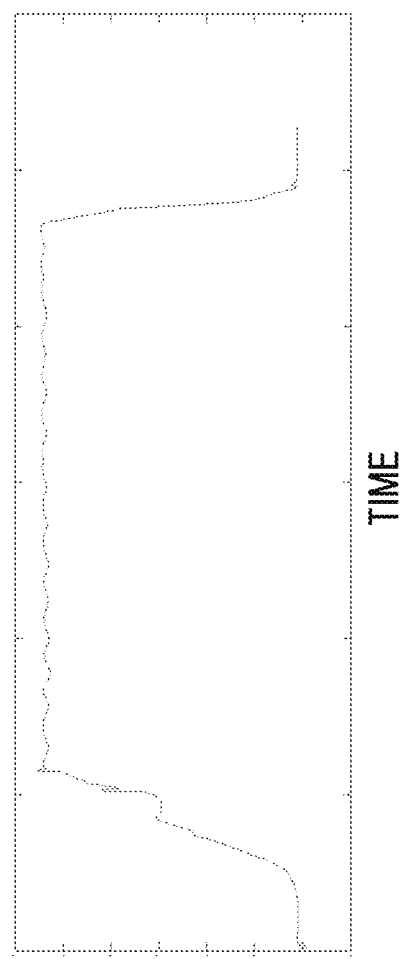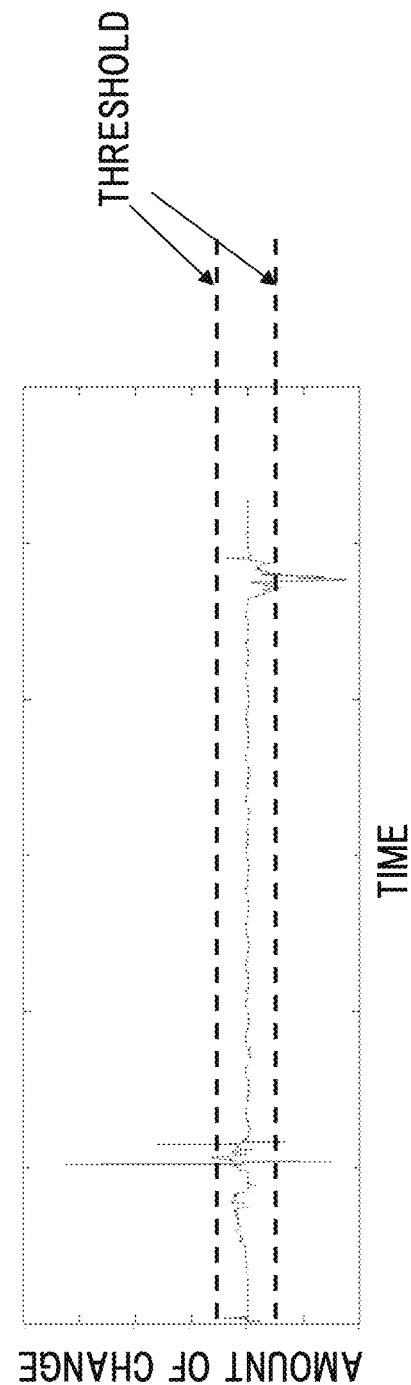

MEDICAL IMAGING APPARATUS INCLUDING BIOLOGICAL SIGNAL PROCESSING SYSTEM, MEDICAL IMAGING SYSTEM, AND BIOLOGICAL SIGNAL PROCESSING METHOD

BACKGROUND OF THE INVENTION

1. Field of the Invention

The present invention relates to a technique for acquiring biological information of a subject under inspection using an inspection apparatus such as a medical imaging apparatus and providing the information to the medical imaging apparatus.

2. Description of the Related Art

In the examination of a subject (mostly a patient) using a medical imaging device such as an MRI (Magnetic Resonance Imaging) apparatus, in order to reduce the influence of artifacts caused by pulsations and breathing movements of the subject, image capturing synchronized with these movements is widely performed. Regarding pulsation and breathing motion of a subject, usually, a measurement device such as an electrocardiograph or a breathing balloon for measuring breathing motion is attached to the subject under examination, and a signal from the measurement device is taken into the imaging apparatus, thereby controlling imaging. When the breathing motion can be accurately grasped, it is also possible to correct the measurement data or the image by using the movement.

However, a measurement device such as a breathing balloon needs to be prepared for setting it to a patient, and the detection of breathing motion may not be performed with high accuracy due to a matter of setting or individual difference of the subject.

On the other hand, in an MRI apparatus, for example, there has been widely used a technique of performing signal acquisition with a target at a position where there is movement of a diaphragm or the like in order to detect breathing movement and monitoring breathing movement. However, in this technique, the imaging time must be extended because the navigation echo should be generated and collected separately from the nuclear magnetic resonance signal for imaging.

On the other hand, Japanese Pat. No. 6,714,006 (Patent Document 1) discloses a camera system for automatically measuring physiological parameters such as pulsation and breathing of a subject, and describes that the camera system is applied to an MRI apparatus and the physiological parameters are automatically measured during examination by the MRI apparatus. In this camera system, before the subject is conveyed into the bore (examination space) of the inspection apparatus, biometric parameters of the subject are measured by a digital camera installed outside the bore to determine a predetermined range of the subject, and then the predetermined range is photographed by a camera arranged distal to the conveyance side with respect to the subject conveyed into the bore to determine a region of interest using the biometric parameters, and physiological parameters are calculated from photographic data of the region of interest.

SUMMARY OF THE INVENTION

As described above, in order to obtain physiological information (motion information) such as breathing motion and pulsation from a subject without contact, it is important to set a region of interest that best reflects the physiological information (motion information), and in particular, in the case of performing respiration gated imaging, it is essential to set the region of interest correctly. However, in Patent Document 1, the region of interest is determined based on the biometric parameter, specifically, the distance between the sternum and the right clavicle of the subject, and if the region of interest is determined only by the biometric parameter such as the size of the subject, the region of interest may be too wide, or narrow. If the region of interest is narrow, positional deviation may occur, and appropriate setting of the region of interest is not secured. In addition, in the technique described in Patent Document 1, in order to acquire biometric parameters, it is necessary to install a camera outside the bore in addition to the camera that photographs the area including the region of interest. That is, two cameras are essential.

It is an object of the present invention to solve the above-mentioned problems of the prior art, and to provide a technique capable of accurately and automatically setting a region of interest for acquiring biological information based on a biological information signal obtained from a subject placed in an examination space in a non-contact manner, thereby making it possible to efficiently perform imaging of a medical image using biological information (motion information), and to reduce time and labor of a doctor, a technician, or the like.

In order to solve the above-mentioned problems, a medical imaging apparatus of the present invention is provided with a biological signal processing system, and the biological signal processing system is provided with a non-contact type biological information measuring unit that is installed in or near an examination space of the medical imaging apparatus and measures a state of a subject under examination, and a signal analyzing unit that processes a biological information signal measured by the biological information measuring unit and calculates a motion of the subject. The biological information measuring unit acquires the biological information signal from a predetermined range of the subject, and the signal analyzing unit includes a region-of-interest selection unit that selects a region of interest, in which the movement of the subject is to be acquired, from among the plurality of regions using biological information signals for each of the plurality of regions included in the predetermined range, and calculates the movement of the subject using biological information signals measured from the region of interest selected by the region-of-interest selection unit.

The medical imaging system of the present invention includes an inspection apparatus, a biological signal processing system including the above-described biological information measuring unit and signal analyzing unit, and an apparatus for displaying a GUI.

Further, the biological signal processing method of the present invention is a biological signal processing method which processes a biological information signal of a subject under examination measured by a non-contact type biological information measuring apparatus installed in or in the vicinity of an examination space of an inspection apparatus, and calculates a movement of the subject. The method includes a step of generating a biological information signal for each of a plurality of regions using the biological information signal measured from a predetermined range of the subject, a step of calculating an index relating to the strength or noise or a movement for each of the biological information signals of the plurality of regions, and a step of selecting a region of interest of the subject for which a movement is calculated, based on the index.

According to the present invention, it is possible to set a position or a region in which the movement of the subject can be accurately captured by the biological information measuring apparatus as a region of interest, and to obtain the movement of the subject with good accuracy by processing the biological information signal collected from the region of interest.

BRIEF DESCRIPTION OF THE DRAWINGS

FIG. 7 shows an example of the analysis result by the signal analyzing unit of the first embodiment.

FIG. 13 is a diagram illustrating an example of the index (time-series change) when there is an abnormality.

FIG. 14A and FIG. 14B are, respectively, a diagram showing an example of the index (two types of time-series changes) when there is an abnormality.

DESCRIPTION OF THE PREFERRED EMBODIMENTS

Embodiments of a biological signal processing system and a medical imaging system including the same of the present invention will be described below with reference to the drawings.

Figure 1:
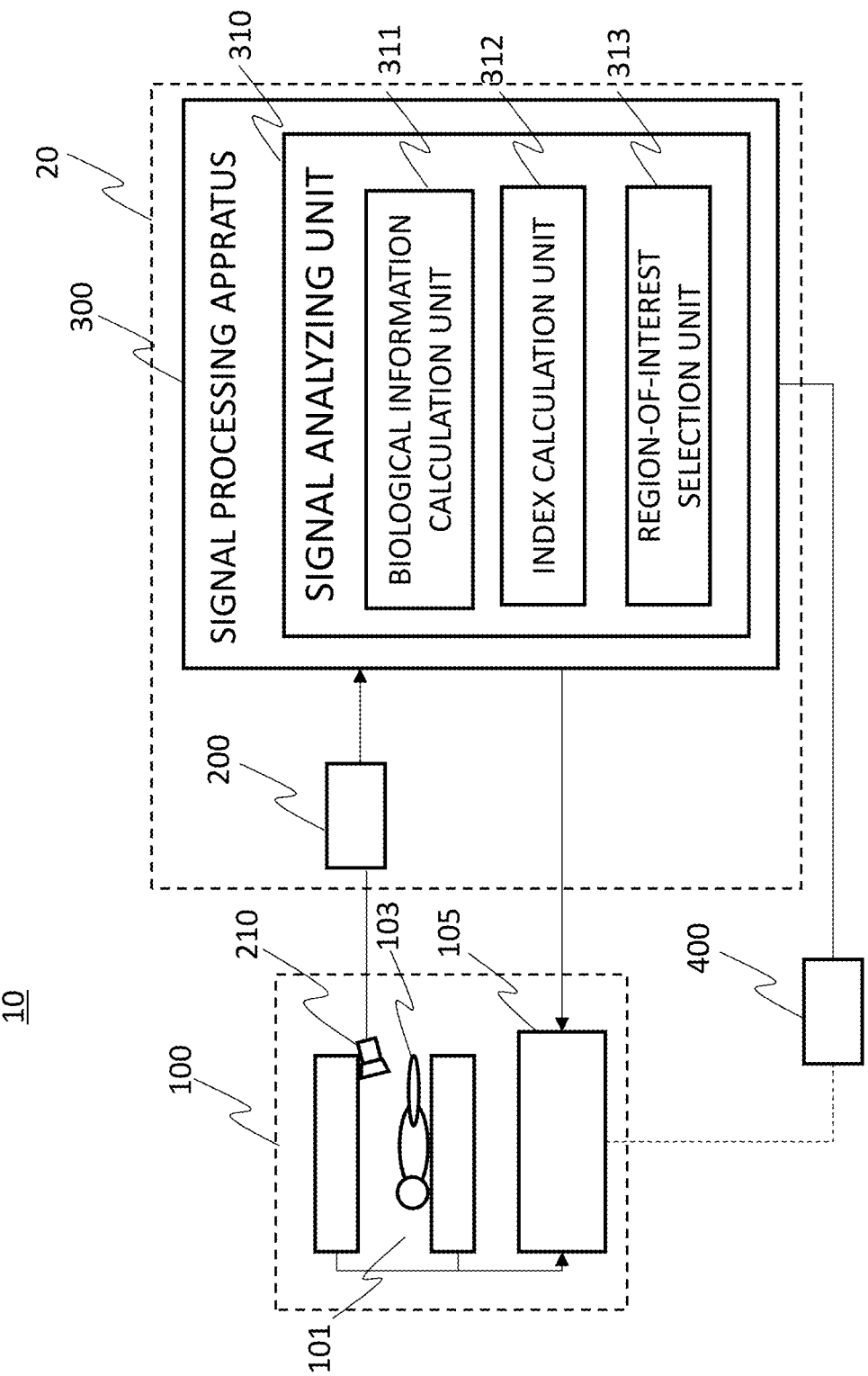
FIG. 1 is a diagram showing an overall outline of a biological signal processing system of the present invention and a medical imaging system including the same.

As shown in FIG. 1, the medical image capturing system 10 mainly includes an inspection apparatus 100, a biological signal measuring apparatus 200, and a signal processing apparatus 300. The examination apparatus 100 is a medical imaging apparatus such as an MRI apparatus, a CT apparatus, or a PET apparatus, and can capture an image using biological information measured by the biological signal measuring apparatus 200. More specifically, the examination apparatus 100 performs synchronous (motion-gated) imaging using the biological information such as pulsation and breathing, correction of measurement data using the biological information, and the like.

The biological signal measuring apparatus 200 is an apparatus for acquiring biological information of a subject under examination using the imaging apparatus 100 without contact, and is composed of a camera, or a distance sensor using an ultrasonic wave, an electromagnetic wave such as infrared rays or millimeter waves, or the like (hereinafter, collectively referred to as a sensor including a camera), detects information relating to a distance between the sensor and the subject or a movement of the subject, and outputs the information as a biological information signal. When the sensor is a camera, video data (time-series image data) obtained by photographing a predetermined range of the subject by the camera is a primary biological (biometric) information signal, and therefrom biological information (secondary biological information signal) representing changes in pixel values and pixel positions over time is generated. The measuring apparatus utilizing electromagnetic waves, ultrasonic waves or the like is provided with a source for generating electromagnetic waves or ultrasonic waves such as millimeter waves and a receiving unit for receiving the reflected waves thereof, and processes the reflected waves from a predetermined range of the subject to generate a biological information signal for each position within the predetermined range.

The signal processing apparatus 300, by using the biological information signal output by the biological signal measuring apparatus 200, performs various processes for determining a site (region of interest) of a subject from which biological information (movement of a subject) to be provided to the imaging apparatus 100 should be acquired. In order to realize it, the signal processing apparatus 300 includes a signal analyzing unit 310. The signal analyzing unit 310 includes a biological information calculation unit 311 that calculates biological information for each of a plurality of positions or regions within the predetermined range from a biological information signal sent from the biometric signal measuring apparatus 200, a region-of-interest selection unit 313 that analyzes the biological information for each position or region and determines a position or region where the most accurate biological information is obtained, an index calculation unit 312 that calculates an index related to noise or intensity of the biological information, and the like.

A signal processing device associated with the imaging apparatus 100 for processing the measurement signal and the image signal in the imaging apparatus 100 may also serve as the signal processing apparatus 300, or the signal processing apparatus 300 may be an independent device for processing the signal of the biological signal measuring apparatus 200. Here, the system including the biological signal measuring apparatus 200 and the signal analyzing unit 310 of the signal processing apparatus 300 is referred to as a biological signal processing system 20. The function of the signal processing apparatus 300 including the signal analyzing unit 310 is realized by a computer including a memory and a processing unit such as a CPU or a GPU reading an analysis program. However, some or all of the functions of the signal processing apparatus 300 may be realized by hardware such as an ASIC, and such a case is also included in the present embodiment. Although not essential, the computer for realizing the function of the signal processing apparatus 300 includes a display 400 for displaying a processing result or a GUI, an input device such as a pointing device or a keyboard, a storage device for storing the above-described analysis program, the processing result, data necessary for processing, and the like, similarly to a general computer. Note that the display 400 for displaying the GUI may be a display provided in the imaging apparatus 100.

Figure 2:
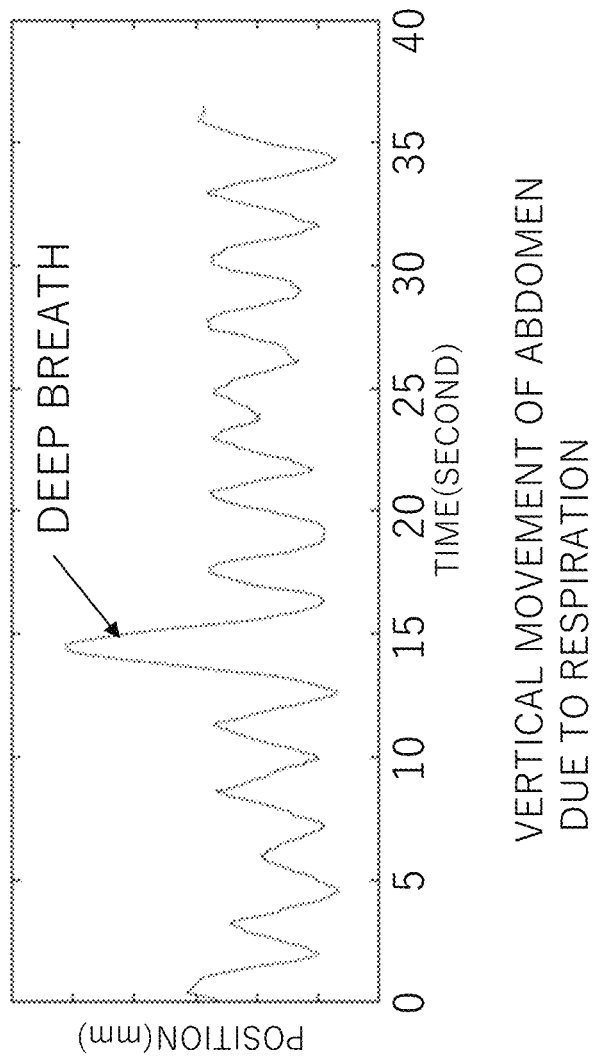
FIG. 2 is a diagram illustrating an example of a biological information signal.

The specific content of the biological information signal will be described later, but in the case where the biological information is periodic movement such as pulsation or breathing of the subject, the secondary biological information signal will be a signal having a periodicity having a predetermined amplitude as shown in FIG. 2. The subject region in which the biological information signal as shown in FIG. 2 is obtained is limited to a relatively narrow range, and even in the vicinity thereof, there are regions in which the noise is large and the periodicity is difficult to determine, and regions in which the amplitude of the signal is small and difficult to determine. Therefore, when the biological information signal as an average value of these regions is obtained, the accuracy of the biological information is deteriorated. In addition, there is an individual difference in an optimum region for acquiring the biological information signal, and even if the biological information signal is determined from the landmark on the subject, it is not always possible to obtain a biological information signal with high accuracy.

The biological signal processing system 20 of the present embodiment first determines an optimal position (region of interest) of a subject for obtaining biological information using the biological information signal measured by the biological signal measuring apparatus 200, and then calculates biological information using the biological information signal obtained from the determined region of interest. In order to determine a region of interest, biological information signals obtained from a plurality of regions are used to calculate indicators related to noise and the intensity of motion. Based on the calculated one or a plurality of indices, a region in which the noise is small and the motion intensity is large is selected from a plurality of regions, and the region is set as a region of interest. There are various ways to set a size and to divide a plurality of regions, and the region of interest to be selected is not only one, but may be 2 or more.

Hereinafter, an embodiment in which the imaging apparatus 100 is an MRI apparatus and the sensor of the biological signal measuring apparatus 200 is the camera 210 will be described.

Embodiment 1

Figure 3:
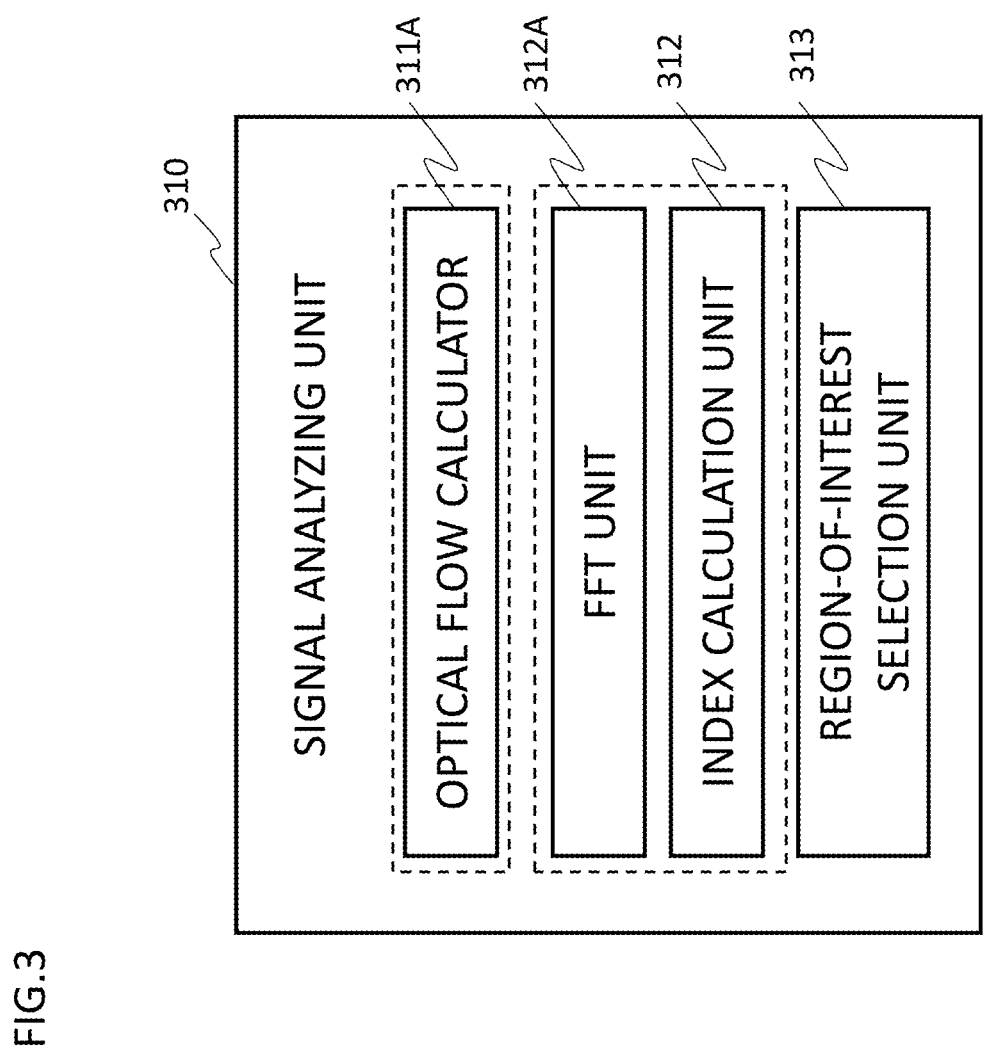
FIG. 3 is a block diagram showing the configuration of the signal analyzing unit of the first embodiment.

In the present embodiment, the sensor of the biological signal measuring apparatus 200 is a single camera, acquires a video signal as a primary biological information signal, and calculates a signal representing a positional variation obtained from an optical flow of an image as a secondary biological information signal. The overall configuration of the apparatus is the same as that shown in FIG. 1. FIG. 3 shows the details of the signal analyzing unit 310. In FIG. 3, elements having the same functions as those shown in FIG. 1 are denoted by the same reference numerals.

As illustrated, the signal analyzing unit 310 includes an optical flow calculating unit 311A that receives a video signal (primary biological information signal) from the sensor (camera) 210 as the biological information calculation unit 311 of FIG. 1, calculates an optical flow from image data of two or more frames adjacent in time, and calculates variations in the subject position for each pixel or for each sub-pixel. The index calculation unit 312 calculates an index representing the noises and the strengths of movements of the biometric signals for each pixel or for each sub-pixel generated by the optical flow calculation unit 311A. The index calculation unit 312 calculates, for example, band power as an index of the strength of motion. For the calculation, the index calculation unit 312 includes an FFT unit 312A that converts the biological signal information into the frequency information. The region of interest selection unit 313 determines a region of interest in which highly accurate biological information signals can be collected using the index calculated by the index calculating unit 312.

Figure 4:
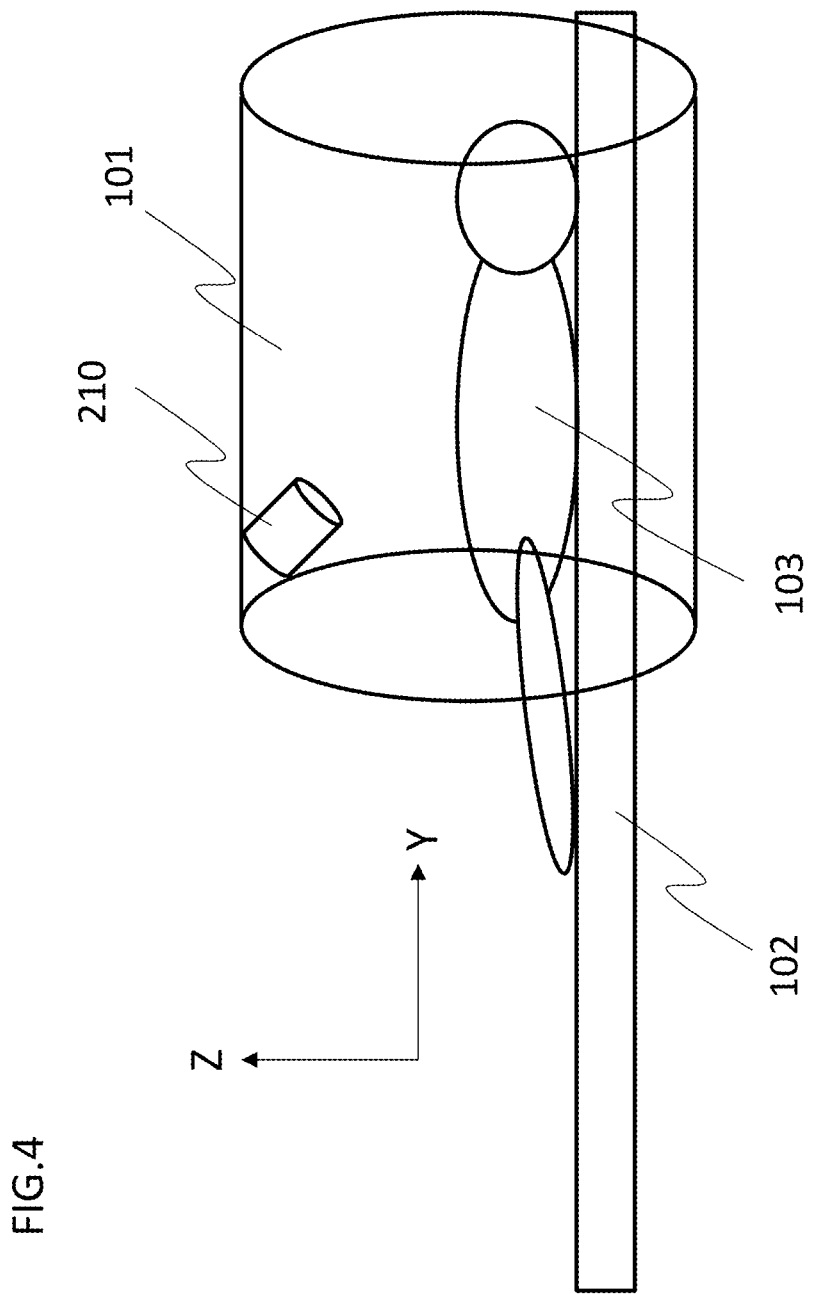
FIG. 4 is a diagram illustrating an example of the installation position of the camera in the inspection apparatus.
Figure 5A:
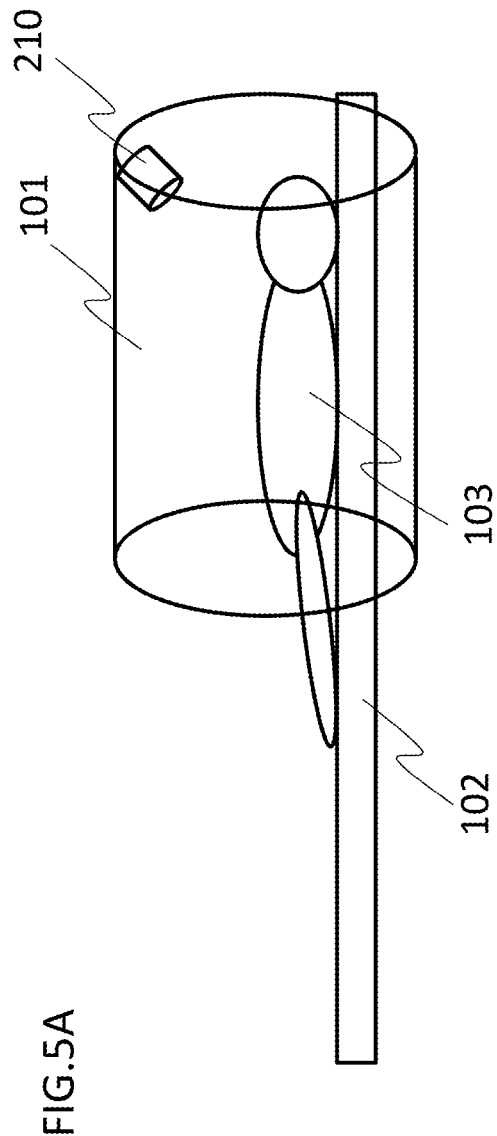
FIG. 5A and FIG. 5B show, respectively, another examples of the installation position of the camera in the inspection apparatus.
Figure 5B:
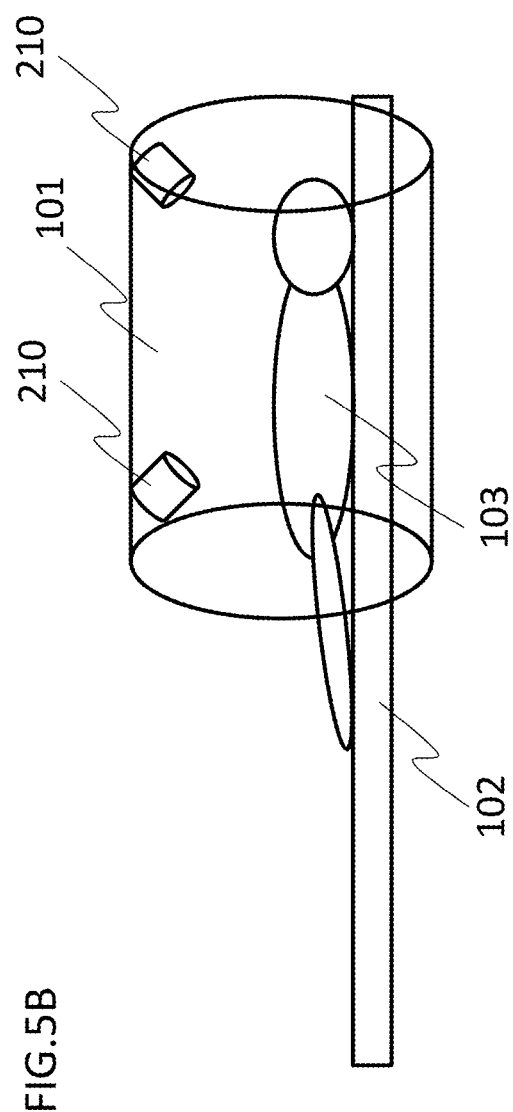

For example, as shown in FIG. 4, in the case of an apparatus such as an MRI apparatus in which the inspection apparatus 100 has an elongated cylindrical bore 101 as an examination space and the subject 103 is placed on the table 102 and arranged in the examination space, the camera 210 is installed at a position where the subject is obliquely imaged from the end in the bore 101 and above the subject 103, and obtains an image of a relatively wide range including the chest of the subject 103. Incidentally, FIG. 4 is an example of attaching the camera 210 to the inlet side for inserting the subject into the bore, but as shown in FIGS. 5A and 5B, the camera may be attached to the opposite side, or on both sides. Two or more cameras may also be installed. As shown in FIG. 5B, by attaching on both sides, it is possible to select and use a camera image suitable for detection of motion. For example, if the entrance camera inserted into the bore is closer to the abdomen and the opposite camera is closer to the face, breathing motion is detected using the entrance camera image and beating (pulsation) is detected using the opposite camera image. Alternatively, breathing motion may be detected using camera images on both sides.

Figure 6:
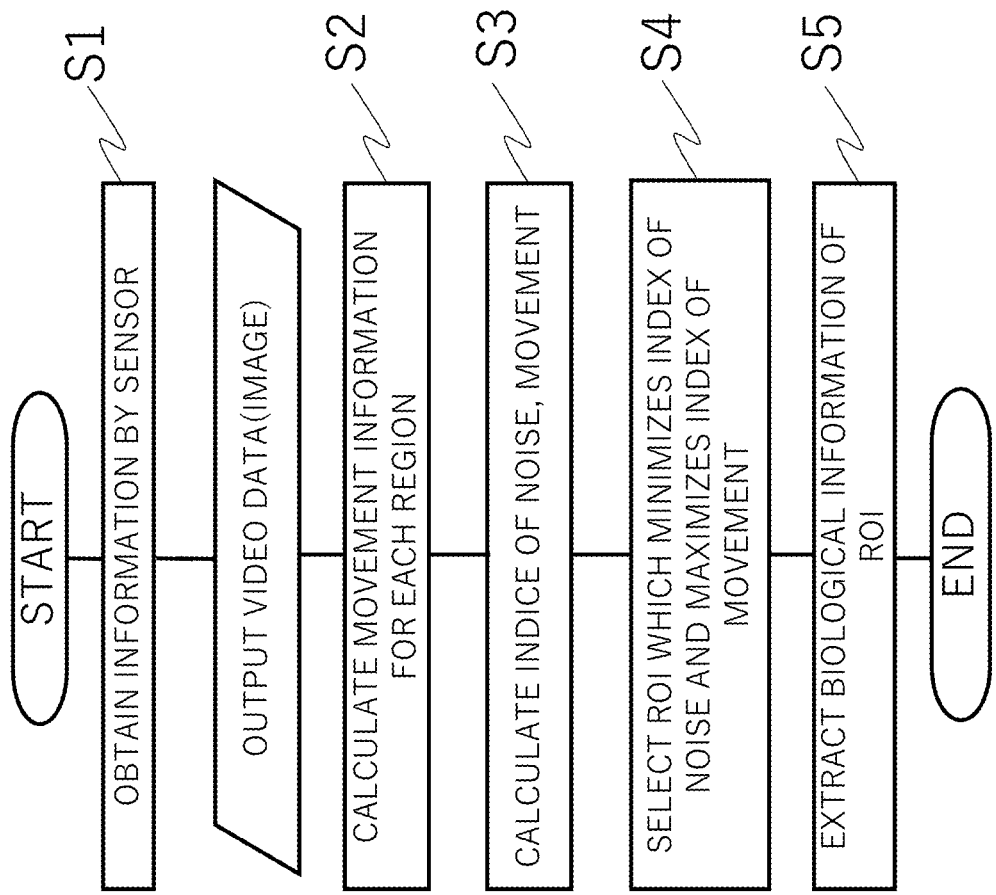
FIG. 6 is a diagram illustrating the flow of operation of the biological signal processing system of the first embodiment.

FIG. 6 shows an outline of the operation of the biological signal processing system 20 in the above configuration. As shown in the figure, prior to imaging by the imaging apparatus 100, measurement by the biological signal measuring apparatus 200 is started, and information from the sensor is acquired (S1). Here, the sensor is a camera, and a video signal is output as a biological information signal. The optical flow calculator 311A receives the video signals and calculates an optical flow, which is motion data, from changes in the images between the frames.

The optical flow is a change in the pixel position between frames for each pixel expressed by a velocity vector, it can be calculated using a gradient method such as, for example, a Lucas-Kanade. By calculating this between each frame, as the integrated value of the velocity vector, it is possible to obtain a variation with respect to the time axis of each pixel (S2). If the body axis direction of the subject 103 is taken as the Y direction, this variation can be obtained as a component (vector absolute value of the Z component) in a direction (Z direction) orthogonal to the Y direction. An example of the variation thus obtained is shown in FIG. 7(A).

Next, among the variations of each pixel (for each position in the image), in order to determine the position of the variation that reflects the body movement to be determined most accurately, the index calculation unit 312 divides the image into a plurality of regions, and calculates indices of noise and movement for variations in each region (S3). In the present embodiment, the standard deviation (SD) of the variation value and the band power (BP) of the variation are calculated as indices. SD is an indicator of noise and is used to eliminate areas where large noise is present. BP is an index for knowing whether or not a large motion has occurred in the frequency band related to the body motion.

To calculate the band power, FFT unit 312A performs Fourier transform the variation with respect to the time axis as shown in FIG. 7(A), to calculate the power for each frequency as shown in FIG. 7 (B). Power can be expressed by Equation (1), and this is integrated by Equation (2) in the frequency band (f1-f2) to calculate the band power. If the motion of interest is breathing (respiration), the period is, for example, 2 to 5 seconds (0.2 to 0.5 Hz), and the power of this band is calculated.

[Equation 1]

$$P(f) = \frac{\Delta t}{N} \left| \sum_{n=0}^{N-1} x_n e^{-j2\pi f \Delta tn} \right|^2 \quad (1)$$

In Equation (1), f is the frequency, x is the sampling measurement signal, N is the number of measurement points, $\Delta t$ is the sampling interval.

[Equation 2]

$$BandPower = \int_{f1}^{f2} P(f) \quad (2)$$

In step S4, the index calculation unit 312 calculates the indices SD and BP for each region, and the region-of-interest selection unit 313 selects, based on the index calculated by the index calculation unit 312, a region in which the noise is small and the motion is large as a region of interest (S4). Here, the minimum unit of the region for which the index calculation unit 312 calculates the index is each pixel, but one region may be selected from roughly divided regions, and the region may be further subdivided to select one or a plurality of regions from the divided regions. Further, areas where the brightness of the image is too high or the brightness is too low may be excluded by setting a threshold in advance, since the calculation of the optical flow and the index is likely to be unsuccessful for those areas. When calculating BP, time information of a certain length or more is required. Compared to BP, SD can be calculated in a relatively short time. Therefore, an index SD may be used first to select a region of interest to start acquisition of biological information, and then an index BP may be used to narrow down the region of interest. Thus, it is also possible to shorten the time until the start of acquisition of biological information.

Further, the calculation formula of the band power described above is not limited to Equations (1), (2). Appropriate calculation equations are used according to the measurement data.

Figure 8B:
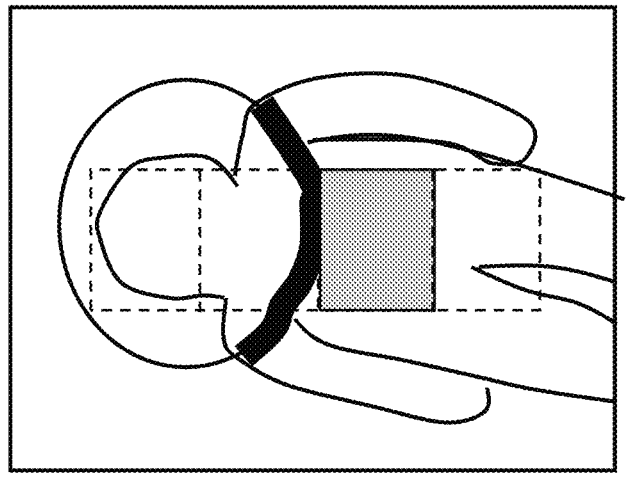
FIG. 8A and FIG. 8B are, respectively, a diagram illustrating selection of a region of interest by the region-of-interest selection unit according to the first embodiment.
Figure 8A:
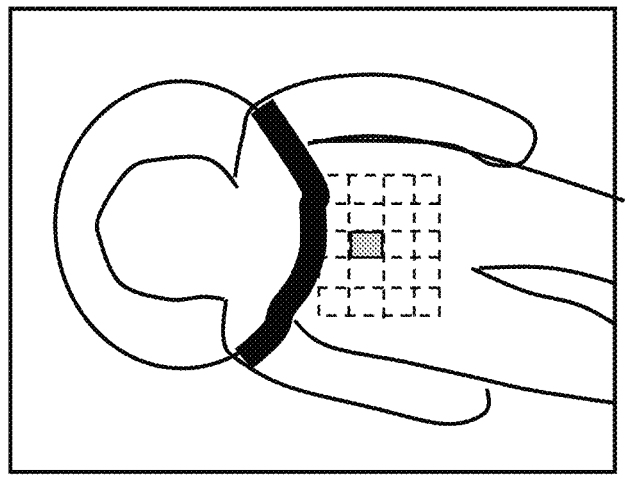

For example, as shown in FIG. 8, first, an index is calculated for each region by dividing a predetermined range of an image (or optical flow map) into relatively large regions 71 to 74 (e.g., 140×140 pixels), a region with high accuracy (region 72 indicated by gray) is selected from a plurality of regions, and the region 72 is divided into a plurality of small regions (e.g., 20×20 pixels) to calculate the index of the small regions. Of these small regions, one or a plurality of regions with the highest precision are regarded as regions of interest. For the calculation of the index of the region, an average value or an intermediate value of the optical flow (variation) of all the pixels included in the region can be used.

Here, an example has been described in which the region is narrowed down by two stages, i.e., a large region and a region with high accuracy, but the region may be set up in one stage if it is desired to set up the region in a shorter time even if the accuracy is somewhat low, or may be set up in three or more stages if it is desired to set up a region with higher accuracy. In addition, although an example in which an optical flow map is formed and then divided into regions has been described here, a region may be limited a little by using an image before the optical flow processing and thereafter the optical flow process may be performed. For example, a region in which there is no obvious living body may be excluded from the region in which the optical flow processing is performed at the stage of the image before the optical flow processing.

The region-of-interest selection unit 313 may select the region of interest using the indices SD and BP by the following method. For example, when the BP is larger than that of other regions, it is considered that periodic body movements are reflected. As for SD, it can be a high value in both cases of large noise other than body movement and cases of large movement. But, it is considered to be a noise when SD is large in spite of small BP or when SD is protruding in comparison with other areas. Therefore, for example, the region of interest selection unit 313 can select a region of interest by first selecting a plurality of regions having a large BP, and excluding a region in which BP or SD exceeds a predetermined threshold.

Further, in order to improve the accuracy of the index value, in particular, the SD, the time-series data of the variation may be subjected to filtering processing or regression processing of an arbitrary order before the index value is calculated. Further, since the waveform of the biological information does not necessarily have perfect periodicity, a typical waveform of the biological information as a target may be prepared and a similar shape may be searched for. When searching for a similar shape, AI such as machine learning may be applied. In addition, a frequency analysis technique using Wavelet transform may be adopted.

Figure 9:
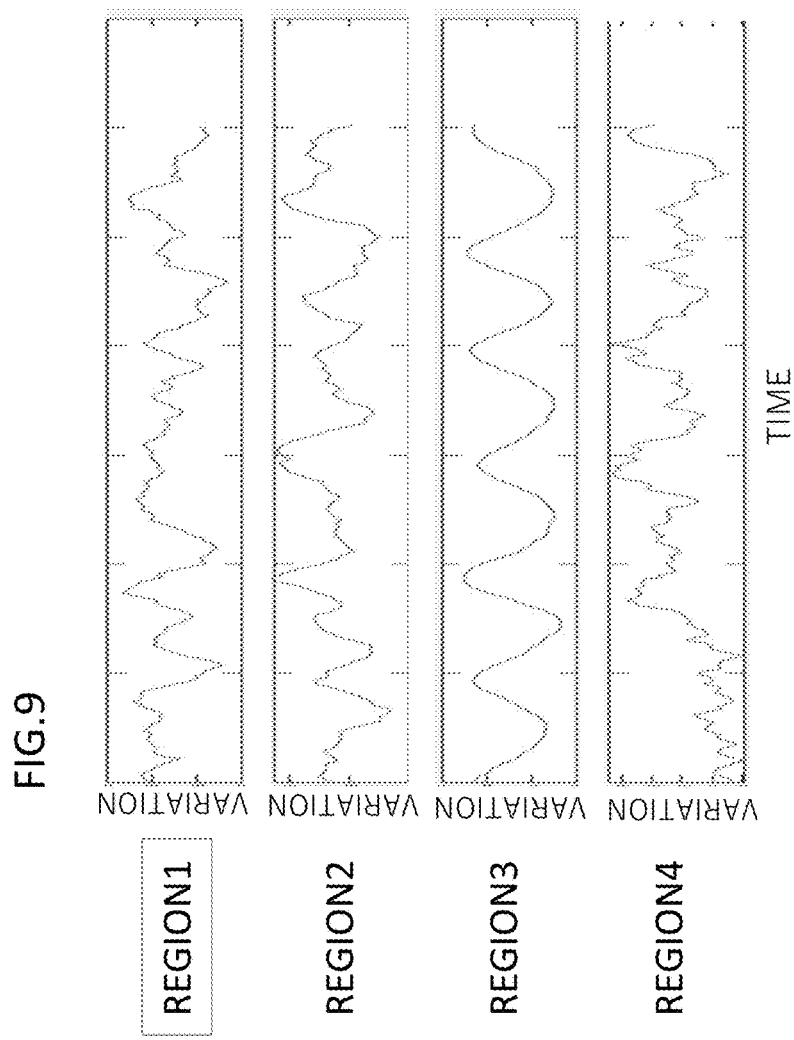
FIG. 9 is a diagram illustrating an example of selection of the region of interest using the index.

As an example, FIG. 9 shows the variation calculated from the optical flow and the results of calculation of SD and BP for the four regions. As shown in the figure, since the region 1 has a large BP and yet remarkably large SD, it is excluded as the noise thereof is large. The region 3 having a large BP is selected as the region of interest in the remaining three regions. This result agrees well with the graph of the variation, and the region reflecting the body motion is set as the region of interest. The threshold values of SD and BP can be set from empirically obtained values.

In the above example, the region-of-interest selection unit 313 selects the region of interest using BP and SD, but it is also possible to use an index such as a ratio of BP and SD. Among factors that increase SD, frequency distribution shown in FIG. 7 (B) is different in noise and body movement. Accordingly, the range of the distribution (e.g., a range of frequencies equal to or higher than a predetermined power) may be also used as an index.

As shown in FIG. 5B, when two or more cameras are used, the above-described indices are calculated using video signals of a plurality of cameras, respectively, and an area of interest is selected for each camera.

When the region of interest is determined by the region-of-interest selection unit 313, the signal analyzing unit 310 uses the video signal sent from the cameras 210 to calculate the variation of the region of interest by the optical flow calculator 311A when the imaging apparatus 100 starts imaging (examination), and sends the calculated variation to the imaging apparatus 100 as biological data (S5). Imaging apparatus (medical imaging apparatus) 100, as shown in FIG. 1, comprising a computer 105 which functions as a control unit for controlling imaging using the biological information and an arithmetic unit for reconstructing the image, performs synchronous imaging using the biological information when performing synchronous imaging. For example, the control unit controls to perform imaging at a constant phase of the variation. Alternatively, the arithmetic unit of the imaging apparatus 100 can correct the acquired image using the movement information of the imaging part. A known method can be employed for the synchronous imaging and the correction using biological information, and description thereof is omitted here.

According to the present embodiment, since the optical flow is calculated from the video signal acquired by the camera, the region of interest in which the biological information with large motion and small noise is accurately obtained is determined, and the biological information from the region of interest is acquired, the biological information (motion of the subject) can be accurately acquired without depending on the region-of-interest setting skill of the examiner or the individual difference of the subject. In addition, since the camera is used, the labor and time required for setting a sensor to the subject or the like can be eliminated.

Although the case where the imaging apparatus 100 is an MRI apparatus has been described as an example, the imaging apparatus may be a medical imaging apparatus other than the MRI apparatus, or the biological signal processing system of the present invention may be applied to an examination apparatus such as an endoscope or an ultrasonic apparatus inserted into the body. In that case, the examination space is to be construed in a broad sense to include supports and struts for supporting the examination apparatus.

It is also possible to display, as a GUI, a graph of the temporal change of body movement such as breathing or the like as shown in FIG. 7 or FIG. 8, or a diagram visualizing the position of an automatically set region on the display 400 in the diagnostic apparatus. Thereby, the technician can grasp the situation of the subject more clearly. Further, since the frequency of the body movement is known by Fourier transform of the variation with respect to the time-axis by the FFT unit 312A, the respiration rate may be calculated from the frequency and displayed on the display.

Embodiment 2

In the first embodiment, the optical flow is calculated using the video signal from the camera, and the optical flow is analyzed to select the region of interest. In the present embodiment, however, a stereo camera is used to analyze the distance from the camera calculated by utilizing the deviation of the image by the left and right cameras to the subject, and select the region of interest.

In the present embodiment, the configuration of the signal processing apparatus 300 is the same as that of the first embodiment except that the optical flow calculator 311A of FIG. 3 replaces a distance calculator, and processing procedure is the same as the procedure shown in FIG. 6. Hereinafter, a description will be given focusing on points different from Embodiment 1.

Figure 10B:
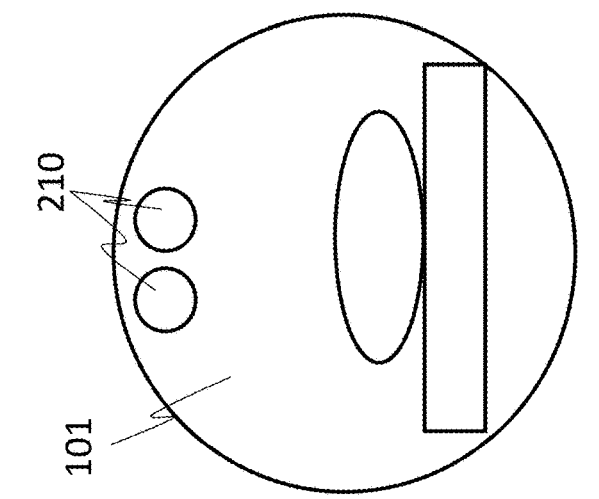
FIGS. 10A-10B are respective diagrams illustrating the arrangement of the camera of the second embodiment.
Figure 10A:
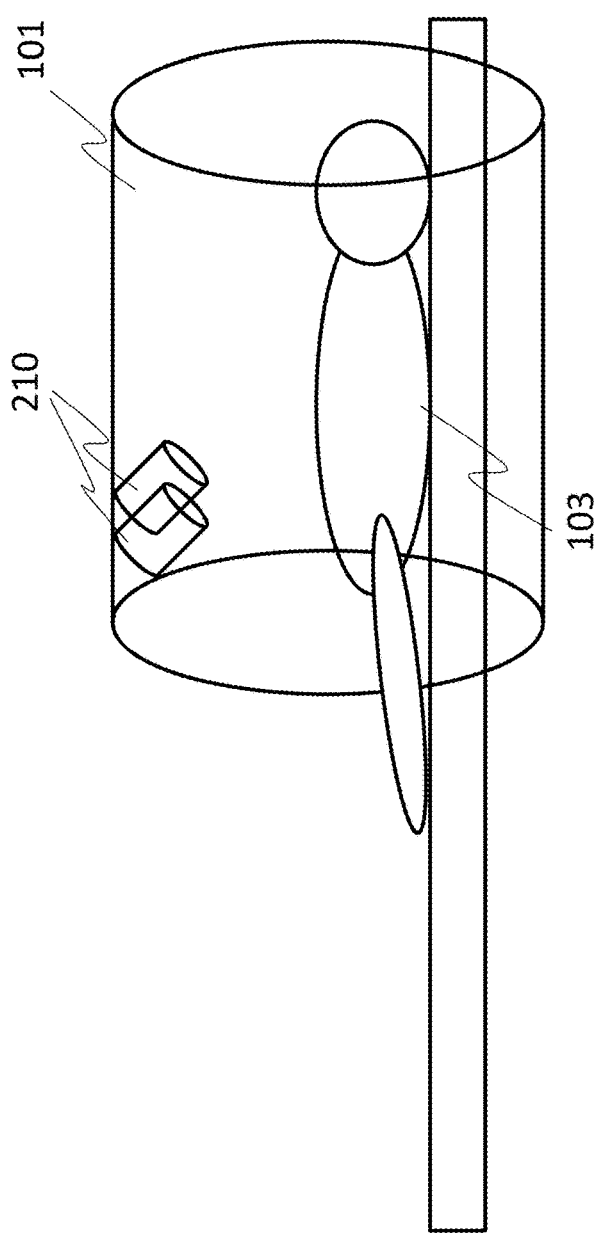

Stereo camera 220, when the body axis direction of the subject is the Y direction and the lateral direction perpendicular thereto is X the direction, as shown in FIGS. 10A-10B, the left and right cameras are installed in the bore so as to be aligned in the X direction.

Signal analyzing unit 310 (distance calculator), when inputting the video signal of the left camera and the right camera of the stereo camera 220, detects the deviation S of the images, for each frame of both video signals, and calculates the distance D from the focal point to the object using the focal length f of both cameras and the reference length B (distance between the focal point and the focal point) according to the following equation (3). [Equation 3]

$$D = B \times f / S \quad (3)$$

The deviation amount S of the images of the left camera and the right camera can be calculated by a method such as block matching. In this case, one image is made to a standard and divided into a plurality of regions. For each region, a region having a high correlation in the other image is determined, and the deviation S between the images is calculated for each frame. Thus, the variation of the distance D for each region is obtained. This variation, similar to the graph shown in FIG. 2 and FIG. 7 (A), becomes biological information reflecting the body movement.

When the variation of the distance between the subject and the camera is calculated by the distance calculator, index calculation unit 312 calculates an indicator of the magnitude of noise and movement using the distance variation for each region. The index may be the standard deviation SD of the variation, the band power BP, or a combination thereof, similarly to Embodiment 1, and can be calculated in the same manner as Embodiment 1. After that, the region-of-interest selection unit 313 selects a region having a small noise and a large motion using the index calculated for each region by the index calculation unit 312, calculates a variation from the selected region of interest, and outputs the variation to the imaging apparatus as a biological information signal, similarly to Embodiment 1.

According to the present embodiment, by using a stereo camera, a distance directly reflecting the body movement can be obtained so that it is possible to perform accurate region selection.

<Modifications>

In Embodiment 1 and Embodiment 1, the case where only one body movement (for example, breathing movement) is obtained as the biological information signal has been described. It is also possible to obtain breathing movement and beating at the same time. As shown in FIG. 7(B), it is possible to determine the power for each frequency by Fourier transform the variation graph. Breathing is about 0.2-0.5 Hz, whereas beating is about 1 Hz~2 Hz, which differs greatly. In the graph reflecting the frequency of body motion, these two body motions appear as peaks of different frequencies.

Therefore, when two body movements are monitored, the index calculation unit 312 calculates BP for each of the two body movements by varying the integration range (band f1-f2) represented by the equation (2), and the region-of-interest selection unit 313 selects the region of interest for each type of body movement based on the calculated BP and SD of the entire variation.

Embodiment 1 and Embodiment 2 use the video signal from the camera, as the biological information measuring apparatus 200. It is also possible to use a ranging meter or the like using a non-contact infrared or millimeter wave. Also in such a case, by obtaining the variation of the distance for each region, it is possible to perform the analysis and selection of the region of interest of the variation using the indicator similarly to Embodiments 1 and 2.

Embodiment 3

Figure 11:
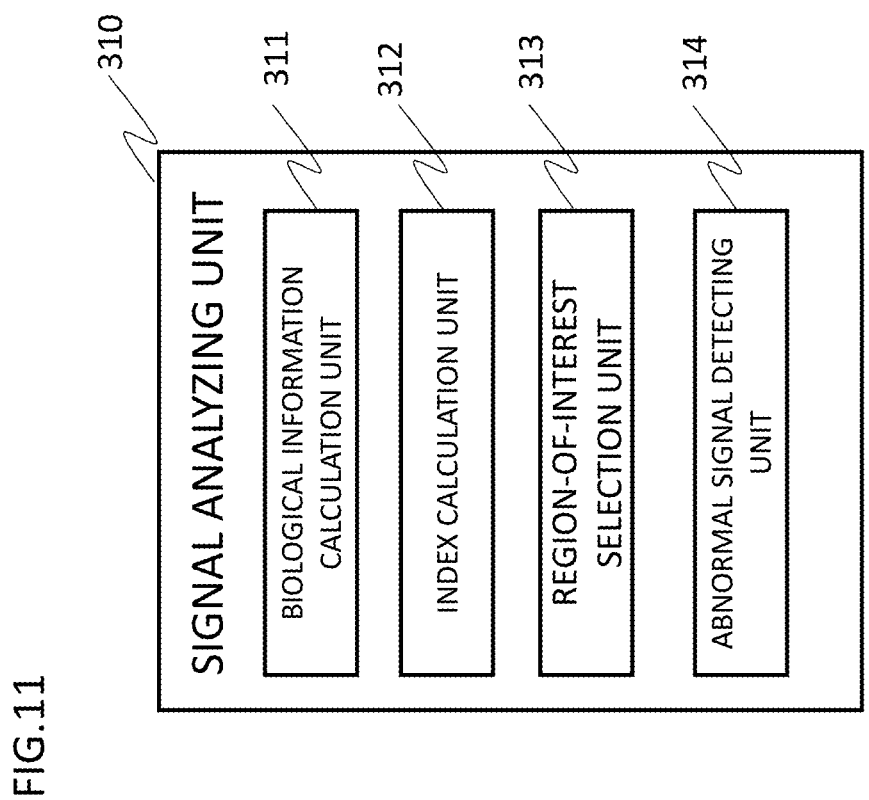
FIG. 11 is a diagram showing a configuration of a signal processing apparatus of the third embodiment.

The biological signal processing system of the present embodiment is characterized in that it deals with not only breathing motion and pulsation but also motion and abnormal situation of a subject that may occur suddenly. The method of acquiring the biological signal may employ any of the methods of the above-described embodiments. Signal processing apparatus 300 (signal analyzing unit 310) of the present embodiment, as shown in FIG. 11, is provided with an abnormality signal detecting unit 314. The rest of the configuration is the same as that of FIG. 3 (or a modification thereof).

Figure 12:
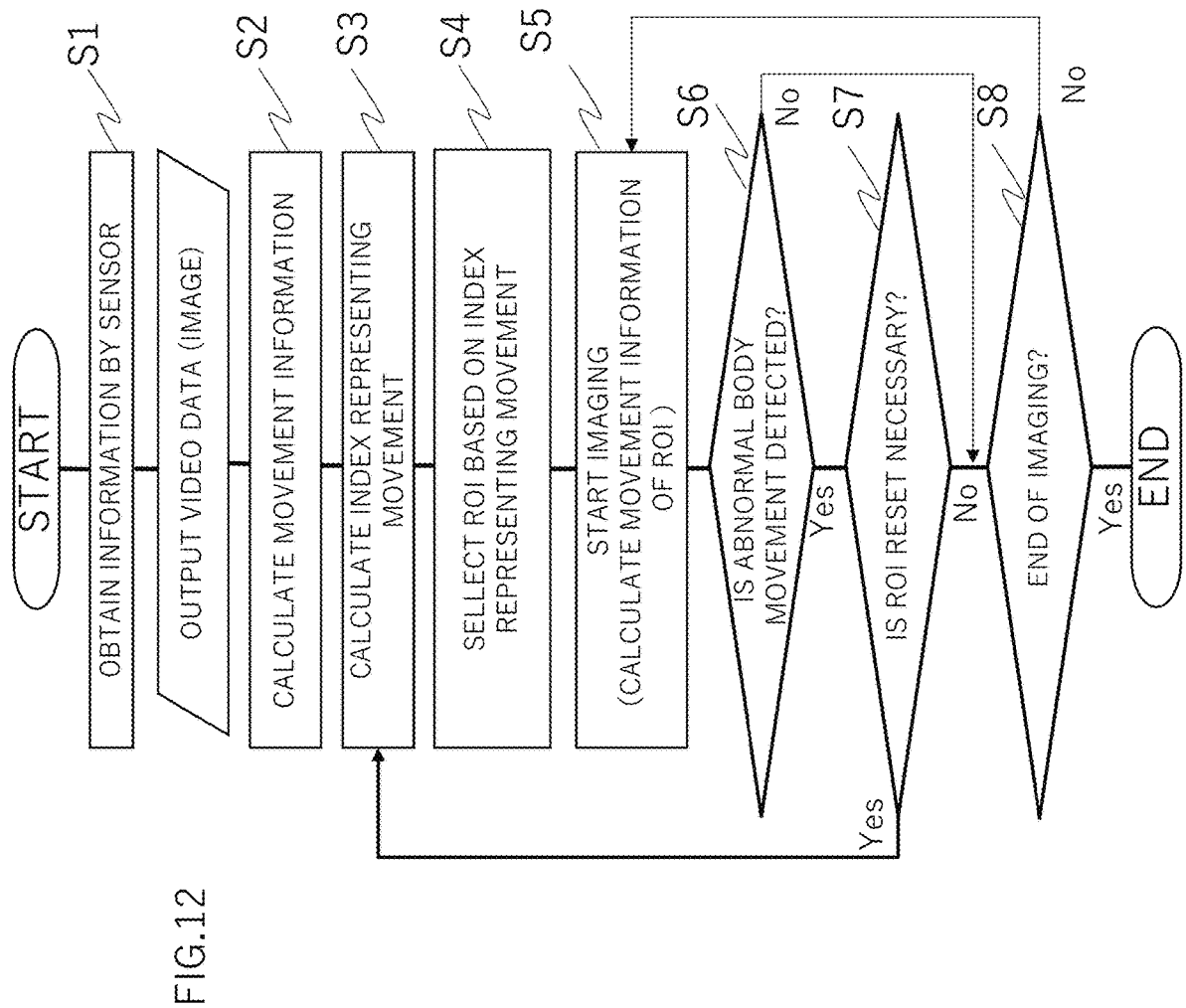
FIG. 12 is a diagram illustrating the flow of operation of the biological signal processing system of the third embodiment.

Hereinafter, the operation of the biological signal processing system according to the present embodiment will be described with reference to the flow of FIG. 12. In FIG. 12, processes having the same contents as in FIG. 6 are denoted by the same reference numerals, and redundant descriptions will be omitted.

Also in the present embodiment, biological information is acquired from the biological signal measuring apparatus 200 (S1), motion information (variation) is calculated (S2), and an index indicating the magnitude of noise and the magnitude of motion is calculated (S3). When the region of interest is selected based on the index (S4), imaging is started, and during imaging, the biological information obtained from the selected region of interest among the biological information acquired by the biological information measuring apparatus 200 is analyzed to calculate motion information (S5). Signal processing apparatus 300 displays this information on the display apparatus 400 provided in the signal processing apparatus 200 or a display device provided in the imaging apparatus 100, and transmits the information to the inspection apparatus (imaging apparatus) 100. In the case of synchronous imaging, as shown in FIG. 2, it is necessary to present the information clearly showing a period of the body movement. Here, in order to enable detection of the abnormality, the scale of display may be changed as shown in FIG. 13. In this case, it is understood that if the subject is in a stationary state, a substantially flat straight line is obtained, and imaging may be continued.

Imaging is performed while referring to such movement information. When there is a large movement, for example, as shown on the right side of the graph of FIG. 13, there is a possibility that the position set as the region of interest may be shifted. The abnormality signal detecting unit 314 determines that there is an abnormality (S6, S7), when the magnitude of the variation exceeds a predetermined threshold value. As a result, the signal analyzing unit 310 repeats the calculation of the motion information (S2) for the plurality of regions, the calculation of the index for each region (S3), and the selection of the region of interest based on the index (S4) through the biological information calculation unit 311 (optical flow calculation unit or distance calculation unit), and sets the newly selected region of interest as the subsequent region of interest.

Thereafter, it is as described above that the imaging is continued while referring to the biological information from the newly set region of interest (S8)

According to the present embodiment, even when an unexpected movement other than the usual body movement of interest occurs, it is possible to immediately update the region of interest, and it is possible to continuously acquire a highly accurate biological information signal.

Further, the amount of change (corresponding to the differential value of the variation) may be used for detecting the unexpected movement, rather than the variation (coordinate information) as shown in FIGS. 14A, 14B. FIG. 14B shows the time change of the amount of change (the differential value of the change). Here, it is also possible to set a certain threshold value, for example, and detect that the change is abnormal when the threshold value is exceeded. The amount of change shown here is the amount of change in the vertical direction (the direction considered to move by breathing) of the drawing, but for example, the amount of change of the component perpendicular to it may also be calculated and the information may be used. Since the vertical component becomes a component which becomes almost 0 in the movement of breathing, there are cases where the abnormality can be detected with higher sensitivity.

The methods of the above-described embodiments and variations can be applied to various imaging fields such as medicine. In addition, the present invention is not limited by the above embodiments and modifications.

What is claimed is:

1. A medical imaging apparatus including a biological signal processing system, the biological signal processing system comprising:
   a biological information measuring unit that is installed in or near an examination space of the medical imaging apparatus, to measure, without contacting a subject under examination, a state of the subject under examination, and that acquires, from a predetermined range of the subject, a biological information signal corresponding to the measurement of the state of the subject under examination; and
   a signal analyzing unit that processes the biological information signal and calculates a motion of the subject, wherein the signal analyzing unit includes
      an optical flow calculation unit which calculates an optical flow using camera images of the subject,
      an index calculation unit which, for each region of a plurality of regions within the predetermined range of the subject, calculates band power of a frequency band of motion obtained from the optical flow, as a corresponding index relating to a strength of the motion in the region, the band power indicating a magnitude of the motion in the region, and
      a region-of-interest selection unit which selects a region of interest, based on, for each region of the plurality of regions, the band power as the corresponding index relating to the strength of the motion in the region, and
   the signal analyzing unit calculates the motion of the subject using the biological information signal measured from the region of interest which is selected from the plurality of regions based on the band power in the region of interest.

2. The medical imaging apparatus of claim 1, wherein the biological information measuring unit includes a rangefinder that generates an electromagnetic wave or an ultrasonic wave and receives the reflected wave to measure a distance.

3. The medical imaging apparatus according to claim 1, wherein the biological information measuring unit includes an image capturing apparatus installed in the examination space, to capture an image obliquely with respect to a predetermined range of the subject.

4. The medical imaging apparatus of claim 1, wherein
   the biological information measuring unit includes a camera, and
   the signal analyzing unit calculates the motion of the subject from a temporal change of an image captured by the camera.

5. The medical imaging apparatus of claim 1, wherein
   the biological information measuring unit includes a stereo camera, and
   the signal analyzing unit calculates a distance between the stereo camera and the subject from image data captured by the stereo camera, and calculates the motion of the subject from a temporal change in the distance.

6. The medical imaging apparatus of claim 1, wherein the biological information signal reflects any of pulsation, beating, and body motion of the subject.

7. The medical imaging apparatus according to claim 1, wherein the index includes any one of (i) a standard deviation (SD) of the biological information signal for each time and (ii) intensity information of the biological information signal.

8. The medical imaging apparatus according to claim 1, further comprises an abnormal signal detecting unit for detecting an abnormal value included in the biological information signal, wherein when the abnormal signal detecting unit detects the abnormal value, the region-of-interest selection unit selects another region of interest.

9. A medical imaging system comprising:
an inspection apparatus having an inspection space in which a subject is disposed;
a biological information measuring apparatus that is installed in or near the inspection space, to measure, without contacting a subject under examination, a state of the subject under examination, and that acquires, from a predetermined range of the subject, a biological information signal corresponding to the measurement of the state of the subject under examination;
a display apparatus that displays a GUI (graphical user interface); and
a signal analysis apparatus that processes the biological information signal and calculates a motion of the subject, wherein the signal analyzing apparatus includes
an optical flow calculation unit which calculates an optical flow using camera images of the subject,
an index calculation unit which, for each region of a plurality of regions within the predetermined range of the subject, calculates band power of a frequency band of motion obtained from the optical flow, as a corresponding index relating to a strength of the motion in the region, the band power indicating a magnitude of the motion in the region, and
a region-of-interest selection unit which selects a region of interest, based on, for each region of the plurality of regions, the band power as the corresponding index relating to the strength of the motion in the region, and
the signal analyzing apparatus calculates the motion of the subject using the biological information signals measured by the biological information measuring apparatus, from the region of interest which is selected from the plurality of regions based on the band power in the region of interest.

10. The medical imaging system of claim 9,
wherein the inspection apparatus is a magnetic resonance imaging apparatus comprising a static magnetic field generating unit for generating a static magnetic field, an imaging unit for applying a high-frequency magnetic field to the subject disposed in a static magnetic field space, receiving a nuclear magnetic resonance signal generated from the subject, and generating an image of the subject using the nuclear magnetic resonance signal, and a control unit for controlling the imaging unit, and
wherein the control unit controls the operation of the imaging unit using the biological information signal from the region of interest of the subject measured by the biological information measuring apparatus.

11. The medical imaging system of claim 9,
wherein the inspection apparatus is a magnetic resonance imaging apparatus comprising a static magnetic field generating unit for generating a static magnetic field, and an imaging unit for applying a high-frequency magnetic field to the subject disposed in a static magnetic field space, receiving a nuclear magnetic resonance signal generated from the subject, and generating an image of the subject using the nuclear magnetic resonance signal, and
wherein the imaging unit corrects the nuclear magnetic resonance signal or the image using the biological information signal from the region of interest of the subject measured by the biological information measuring apparatus.

12. The medical imaging system of claim 9,
wherein the display apparatus for displaying the GUI displays at least one of the plurality of regions and the region of interest selected by the region of interest selection unit as a GUI.

13. The medical imaging system of claim 9,
wherein the display apparatus for displaying the GUI displays at least one of the biological information signal measured by the biological signal measuring apparatus, an analysis result of the signal analyzing apparatus, and data in progress of analysis.

14. A biological signal processing method for processing a biological information signal of a subject under examination measured by a non-contact type biological information measuring apparatus that is installed in or near an examination space of an examination apparatus to calculate a motion of the subject, comprising the steps of:
generating biological information signals for each of a plurality of regions using the biological information signals measured from a predetermined range of the subject;
calculating an optical flow using camera images of the subject and, for each region of the plurality of regions, calculating band power of a frequency band of motion obtained from the optical flow, as a corresponding index relating to a strength of the motion for the region, the band power indicating a magnitude of the motion in the region; and
selecting from the plurality of regions, and based on, for each region of the plurality of regions, the band power in the region, a region of interest of the subject, for calculating said motion of the subject.

* * * * *